United States Patent
Cox

(10) Patent No.: US 11,141,205 B2
(45) Date of Patent: Oct. 12, 2021

(54) DEVICE FOR AND METHOD OF TREATING ACROMIOCLAVICULAR JOINT DISLOCATIONS

(71) Applicant: Wesley Cox, Fayetteville, AR (US)

(72) Inventor: Wesley Cox, Fayetteville, AR (US)

(73) Assignee: XTREME ORTHOPEDICS LLC, Fayetteville, AR (US)

( * ) Notice: Subject to any disclaimer, the term of this patent is extended or adjusted under 35 U.S.C. 154(b) by 364 days.

(21) Appl. No.: 16/020,691

(22) Filed: Jun. 27, 2018

(65) Prior Publication Data

US 2018/0368895 A1 Dec. 27, 2018

Related U.S. Application Data

(60) Provisional application No. 62/525,267, filed on Jun. 27, 2017.

(51) Int. Cl.
*A61B 17/80* (2006.01)
*A61B 17/82* (2006.01)

(52) U.S. Cl.
CPC ...... *A61B 17/8061* (2013.01); *A61B 17/8004* (2013.01); *A61B 17/82* (2013.01); *A61B 17/808* (2013.01)

(58) Field of Classification Search
CPC .. A61B 17/8061; A61B 17/82; A61B 17/0401
See application file for complete search history.

(56) References Cited

U.S. PATENT DOCUMENTS

2013/0123841 A1* 5/2013 Lyon .................... A61B 17/683
606/232
2013/0172944 A1* 7/2013 Fritzinger .......... A61B 17/0401
606/286

OTHER PUBLICATIONS

Acumed LLC, "Surgical Technique Clavicle Plating System, Acu-Sinch Repair System," Hillsboro, Oregon; Effective Dec. 2013.
Mazzocca M.D., Augustus et al., "Anatomic Coracoclavicular Reconstruction Surgical Technique," Arthrex (www.arthrex.com) Published 2012.
Springerplus, Central Figure 1, PubMed 2016: 5(1) Published online Oct. 22, 2016.
Arthrex, "Clavicle Plate and Screw System," (www.arthrex.com) Published 2015.
Milewski et al., MD, "Complications related to anatomic reconstruction of the coracoclavicular ligaments," Am J Sports Med, Jul. 2012; 40(7): 1628-34 Epub May 2, 2012Cox.

(Continued)

*Primary Examiner* — Olivia C Chang
(74) *Attorney, Agent, or Firm* — Kutak Rock LLP; Brian L. Main

(57) ABSTRACT

A device that allows for the predictable/guided anatomic drilling of claviclular tunnels for graft, suture, or combined graft/suture reconstruction of the AC joint is provided. The device simultaneously allows for larger clavicle tunnels which permit graft passage while providing protection, via stress shielding, of the bone between and adjacent to the bone tunnels. In this way, the surgeon is able to utilize anatomically placed clavicular tunnels large enough for graft passage (which reduces the mechanical failure rate of the reconstruction and most closely replicates normal anatomy) while reducing the risk of clavicle fracture, which has plagued other "anatomic reconstruction" techniques.

7 Claims, 3 Drawing Sheets

(56) References Cited

OTHER PUBLICATIONS

Ma et al., Richard, "Managing and recognizing complications after treatment of acromioclavicular joint repair or reconstruction," Curr Rev Musculoskelet Med. Mar. 2015; 8(1); 75-82 Published online Feb. 8, 2015.

Martetschlager et al., Frank, "Complications After Anatomic Fixation and Reconstruction of the Coracoclavicular Ligaments," The American Journal of Sports Medicine; EPubSep. 5, 2013.

Xue et al., C., "Clavicle and caracoid process drilling technique for truly anatomic coracoclavicular ligament reconstruction," Injury Oct. 2013; 44 (10) EPub Jul. 19, 2013.

\* cited by examiner

DEVICE FOR AND METHOD OF TREATING ACROMIOCLAVICULAR JOINT DISLOCATIONS

CROSS-REFERENCE TO RELATED APPLICATIONS

This application claims priority pursuant to 35 U.S.C. 119(e) to co-pending U.S. Provisional Patent Application Ser. No. 62/525,267, filed Jun. 27, 2017, the entire disclosure of which is incorporated herein by reference.

FIELD OF THE INVENTION

The present invention relates generally to medical devices. More specifically, the present invention is concerned with a clavicle plate that is configured to facilitate treatment of acromioclavicular joint dislocations.

BACKGROUND

Injuries to the acromioclavicular (AC) joint are very common. AC joint dislocations account for approximately 8% of all joint dislocations in the body. The severity of the injury determines the most appropriate treatment. Because the majority of the injuries occur in young athletic populations, the ability to restore function and provide predictable pain relief is critically important.

Fortunately, the anatomy of the coracoclavicular (CC) ligaments (Conoid and Trapezoid) and the AC joint capsule is well defined, as are their roles in both normal and injured shoulders. Much work has been done to define the biomechanical responsibilities of the Conoid and Trapezoid Ligaments. These works have successfully provided surgeons with a clear understanding of both the topographical and biomechanical characteristics of these ligaments. The different orientation of the two components has proven to account for different functions. As our understanding of these elements has improved, techniques designed to reconstruct injured CC ligaments have evolved and while many have offered hope and some have offered function, all have offered unacceptably high complication rate.

There are over 60 different techniques described to treat AC joint dislocations. This abundance of techniques reflects the inability for any singular technique to be seen as the "gold standard". Fueled by the seriousness of AC joint injuries, the effects AC joint injuries has on those with them, and the high complication rates of previously known techniques, the orthopedic industry continues to strive to create a gold standard technique for AC joint dislocation treatment.

In 1972, Drs. Weaver and Dunn first described a soft tissue based procedure to reconstruct the CC ligaments. Although this technique was abandoned because of a high rate of graft failures and other complications, it laid the foundation for new techniques to be developed. Unfortunately, previous attempts to eliminate such complications, such as by more accurately replicating the native ligaments with tendon grafts, has created additional complications, such as an unacceptably high rate of bone fracture. For instance, to accurately replicate the native ligaments with tendon grafts, two holes must be drilled through the clavicle, with one hole being positioned near a posterior edge of the clavicle and the other hole being positioned closer to an anterior edge of the clavicle. Consequently, the overall strength of the clavicle is weakened, increasing the risk of clavicle fracture at either hole and/or between the holes.

Efforts to reduce the incidence of clavicle fractures in anatomic AC joint reconstruction fail to resolve the initial complications. For instance, additional middle-ground techniques have been described which allow smaller tunnels, or a singular tunnel to be utilized. Unfortunately, because these techniques do not adequately restore the normal anatomy, they do not adequately restore normal tensions and stresses on the AC joint and subsequently they too have an unacceptably high complications and/or failure rates.

Consequently, it would be beneficial to have a device for and/or a method of replicating the native ligaments with tendon grafts and/or otherwise reducing complications associated with reconstruction of AC joints while reducing the risk of clavicle fracture.

Clavicle plate and screw systems of the prior art are used to assist with healing of clavicle fractures. Specifically, the clavicle plates are secured to the clavicle on each side of the fracture such that the plate spans the fracture, thereby replacing the structural rigidity of the clavicle that had been lost due to the fracture. Some such plates further provide features for coracoclavicular (CC) ligament support. Such ligament support, however, fails to accurately replicate the native ligaments.

Previously known methods for accurately replicating native ligaments are time consuming and labor intensive. For instance, extensive measurements must be taken and analyzed to determine how to replicate the native ligaments. Upon obtaining precise measurements, a surgeon must utilize this information to locate and orient a drill relative to a clavicle. Unfortunately, much of the precision of the measuring step can be lost in the drilling step, increasing associated risks. Furthermore, even if the drilling step is completed with perfect precision, the clavicle is left weakened and vulnerable. Furthermore still, some techniques require the drilling step to drill oversized holes to accommodate screws, such as interference screws, for anchoring or otherwise affixing sutures relative to the clavicle, thereby further weakening the clavicle. Consequently, it would be beneficial to utilize a clavicle plate to reinforce the weakened clavicle. Furthermore, it would be beneficial if the clavicle plate was configured so as to assist the surgeon in locating the plate onto the clavicle. Furthermore still, it would be beneficial if the clavicle plate included one or more feature for assisting a surgeon in drilling one or more hole through the clavicle. Furthermore yet, it would be beneficial if precise measurements were built into the configuration of the clavicle plate such that utilization of the clavicle plate facilitates accurate replication of native ligaments. Furthermore still, it would be beneficial if the clavicle plate included one or more feature for affixing sutures relative to the clavicle.

SUMMARY

The present invention comprises a device for and a method of treating acromioclavicular (AC) joint dislocations. The device is a plate like device (a "clavicle plate" or a "plate") which could be made of any appropriate material. In some embodiments, the clavicle plate includes one or more positioning feature designed to allow the user to quickly and easily determine the correct placement of the device. In some such embodiments, the positioning feature is a mark, such as a centerline or other mark. In some embodiments, the location of the positioning feature on the clavicle plate is determined based on osteologic analysis of human clavicles.

The clavicle plate defines two apertures, the first aperture being associated with an anatomical location of the native Conoid Ligament and the second aperture being associated with an anatomical location of the native Trapezoid Ligament. In this way, the spacing between the first and second apertures represents the anatomic spacing between the native ligaments.

In some embodiments, each aperture is configured to interface with an appropriate sized drill guide, thereby assisting the user in drilling respective first and second holes through the clavicle. Each of the first and second holes (also referred to as bone tunnels) is configured to allow for suture, graft, or combination suture/graft passage. Because the anatomic spacing between the native ligaments is replicated with the aperture spacing, it is also replicated with the drill hole spacing, thereby reducing complications associated with reconstruction of AC joints.

Unlike other techniques, the present invention facilitates perfect/anatomical placement of the clavicular bone tunnels without requiring the end user to make "complex osteologic measurements" in order to place the tunnels in the appropriate location. This is because the clavicle plate of the present invention has these complicated measurements built into it.

The clavicle plate of the present invention is configured to be selectively secured to a clavicle of a patient. In this way, the first and second apertures are capable of being retained in position relative to the clavicle prior to a user drilling respective first and second holes.

The present invention further includes methods of treating AC joint dislocations and other injuries associated with the clavicle, such as by using the clavicle plate of the present invention to assist with drilling, aligning, and/or supporting the clavicle. The present invention further includes methods of treating clavicle fractures and other injuries and/or problem areas associated with the clavicle, such as by securing the clavicle plate of the present invention to a clavicle such that the clavicle plate provides structural support to the clavicle, thereby allowing the clavicle to heal and/or to prevent damage to the clavicle.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention and various features thereof.

BRIEF DESCRIPTION

A preferred embodiment of the invention, illustrative of the best mode in which the applicant has contemplated applying the principles, is set forth in the following description and is shown in the drawings and is particularly and distinctly pointed out and set forth in the appended claims.

Figure 3A:
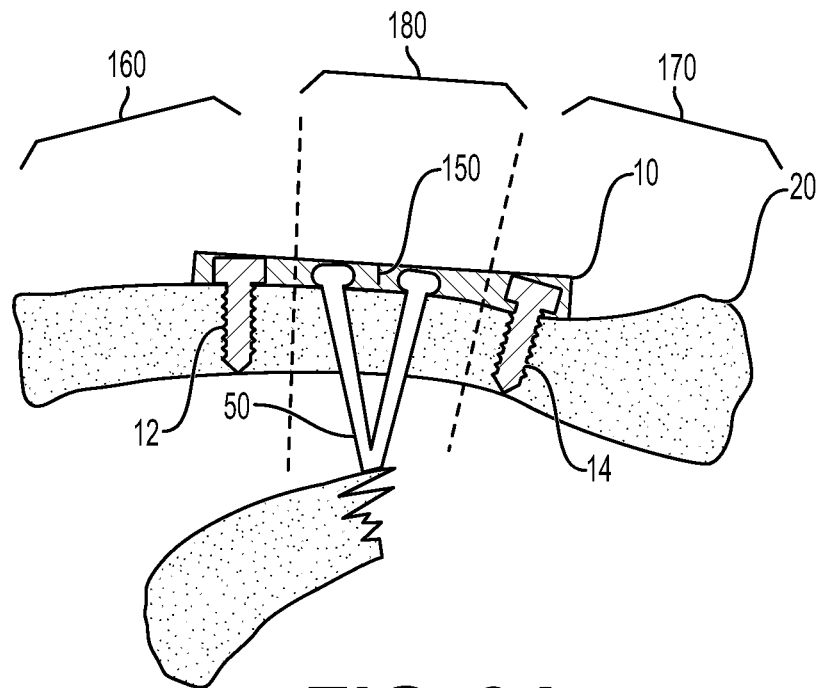
FIG. 3A is a visual representation of a clavicle plate of the present invention being affixed to a clavicle of a patient and anchored to a coracoid of the patient.
Figure 3B:
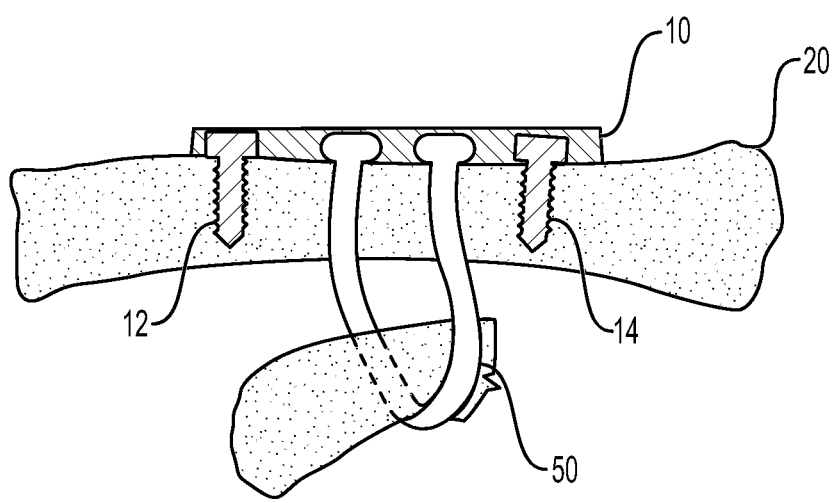
FIG. 3B is a visual representation of a clavicle plate of the present invention being affixed to a clavicle of a patient, FIG. 3B further showing a tendon extending from the clavicle plate and wrapping around a coracoid of the patient, the tendon being secured to buttons associated with the clavicle plate.
Figure 3C:
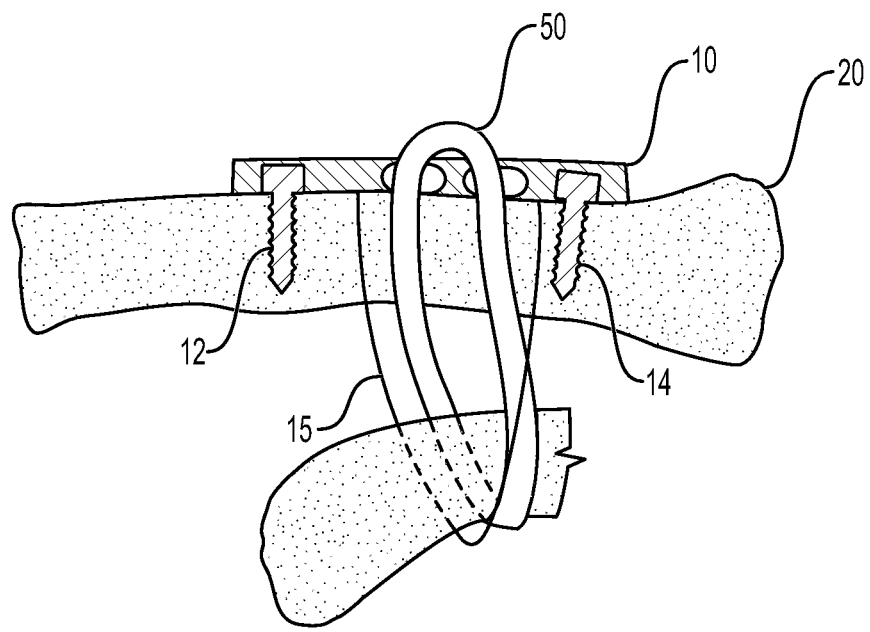

FIG. 3C is a visual representation of a clavicle plate of the present invention being affixed to a clavicle of a patient, FIG. 3C further showing a tendon wrapping around the clavicle plate and a coracoid of the patient and a suture extending from the clavicle plate and wrapping around the coracoid, the tendon extending through first and second apertures of the plat and the ends of the suture extending into small apertures of the plate.

Figure 3D:
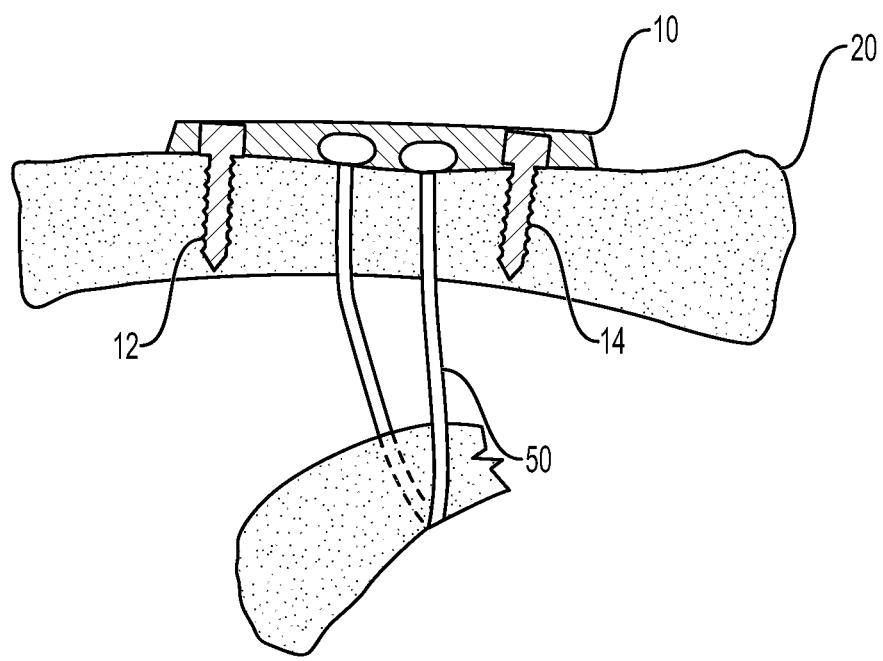

FIG. 3D is a visual representation of a clavicle plate of the present invention being affixed to a clavicle of a patient, FIG. 3D further showing a suture extending from the clavicle plate and wrapping around a coracoid of the patient, first and second ends of the suture extending into respective first and second apertures of the clavicle plate.

DETAILED DESCRIPTION

As required, a detailed embodiment of the present invention is disclosed herein; however, it is to be understood that the disclosed embodiment is merely exemplary of the principles of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
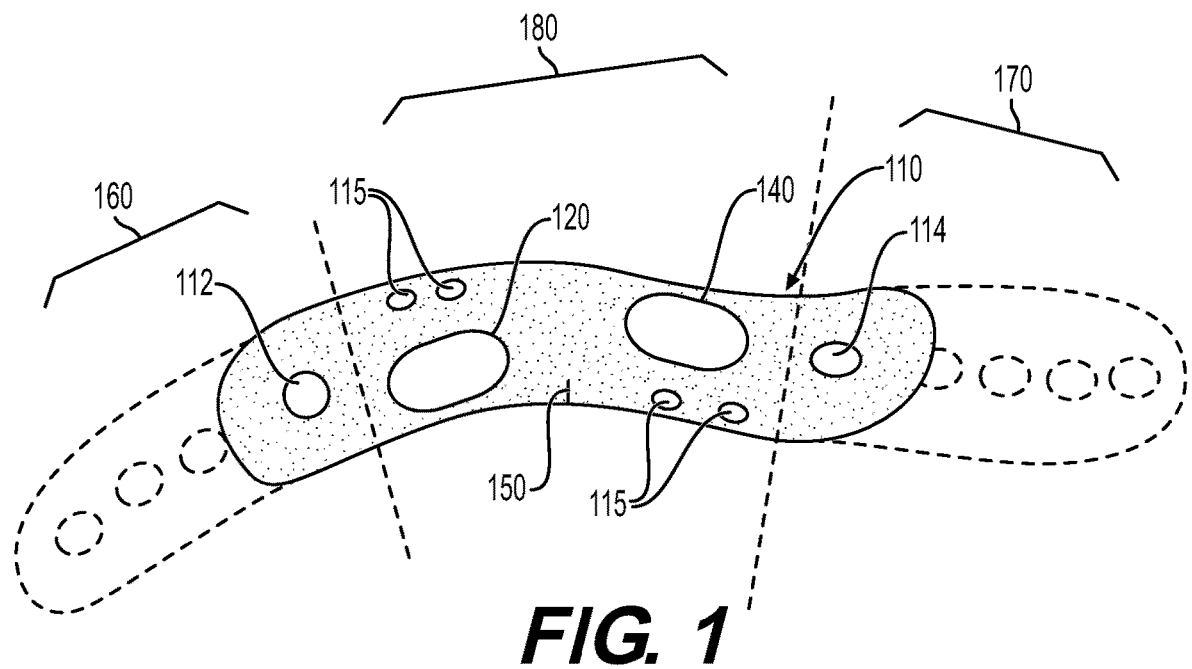
FIG. 1 is a top plan view of a clavicle plate of the present invention showing different lengths in dashed lines.
Figure 2A:
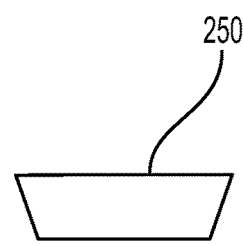
FIG. 2A is a side elevation view of a tapered button of the present invention.
Figure 2B:
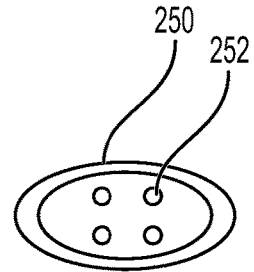
FIG. 2B is a bottom plan view of a tapered button of FIG. 2A.
Figure 2C:
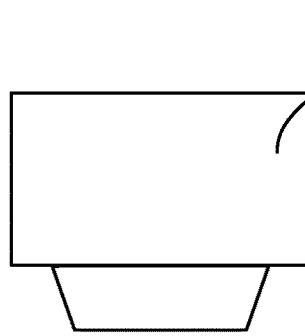
FIG. 2C is a side elevation view of a drill guide that is configured to be used with the clavicle plate of the present invention.
Figure 2D:
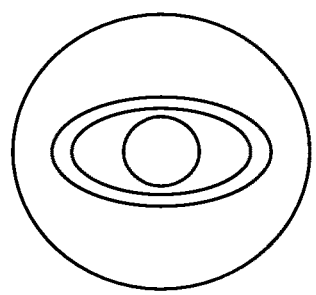
FIG. 2D is a bottom plan view of the drill guide of FIG. 2C.

Referring to FIGS. 1 and 3A, some embodiments of the clavicle plate 10 include a main body 110 defining first 112 and second 114 fastening features, such as screw holes or the like, for securing the plate to a clavicle 20 of a patient. In some such embodiments, the first and second fastening features are configured to receive or otherwise engage with respective first 12 and second 14 fastening devices, such as locking or non-locking screws, for clavicular fixation. In some embodiments, each fastening device is a fastening screw having a diameter ranging from 3.5 mm to 4.0 mm. In some embodiments, the first and second fastening features are defined by respective first portion 160 and second portion 170 of the main body. In some embodiments, first portion 160 and second portion 170 of the main body extend from opposed ends of a third portion 180 of the main body. In some embodiments, each of the first and second portions is configured to be secured to respective first and second regions of a clavicle such that the third portion 180 of the main body spans a third region of the clavicle. In this way, the main body of the clavicle plate is configured to replace loss of structural integrity of the clavicle, such as through a break, a reduction of material (such as through the creation of one or more bone tunnel), or other reduction of structural integrity of the clavicle.

In some embodiments, the main body defines first 120 and second 140 apertures. In some embodiments, each of the first and second apertures is associated with an anatomical location of a ligament of the patient. In some embodiments, the first and second apertures of the clavicle plate are each defined by the third portion of the main body.

In some embodiments, the first and second apertures are configured for facilitating the creation of bone tunnels and/or otherwise facilitating graft/suture passage through one or more bone tunnel. In some embodiments, the first and second apertures are configured to interface with appropriate sized drill guides 25, thereby assisting the user in creation of respective first and second bone tunnels through the clavicle. In some such embodiments, the drill guide(s) and the first and/or second apertures include corresponding interface features for positioning and orienting the drill guide(s) relative to the clavicle, thereby facilitating the positioning and vectoring of the bone tunnels. In some embodiments, the main body is configured to interface with a plurality of drill guides and/or other devices now know or later developed, such as by way of the first and/or second aperture or otherwise.

In some embodiments, the main body defines one or more fixation feature 115 for selective engagement with one or more fixation device 15, such as sutures utilized in repair of surrounding soft tissue, thereby providing potential fixation points for such fixation devices. In some such embodiments, one or more fixation feature comprises one or more small aperture.

In some embodiments, the first aperture is associated with a conoid ligament of the patient. In some such embodiments, a second fixation feature is positioned anterior to the first aperture.

In some embodiments, the second aperture is associated with a trapezoid ligament of the patient. In some such embodiments, a first fixation feature is positioned posterior to the second aperture. In some embodiments, the first 120 and/or second 140 apertures are configured to receive a button 250. In some embodiments, the button and the first and/or second apertures include corresponding interface features. In some such embodiments, walls of the first and/or second aperture are tapered inward so as to define a bottom opening that is smaller than an opposed top opening. In some such embodiments, the button defines corresponding tapered side walls such that the button is capable of being moved in and out of the first and/or second aperture through the top opening but is incapable of passing through the bottom opening. In this way, the button is moveable to a seated configuration by moving the button in a first direction relative to the main body of the plate until the corresponding interface features prevents the button from moving any further. In some embodiments, the button and main body are configured such that biasing the button in a first direction while the first button is in a seated configuration prevents or otherwise inhibits the first button from moving away from a seated configuration. In some embodiments, moving the first button in a second direction causes the first button to move from the seated configuration to an unseated configuration.

In some embodiments, the button 250 defines one or more engagement feature 252 so that it is capable of being utilized for graft/suture placement. In some such embodiments, the one or more engagement feature 252 is a hole or pattern of holes, such as a pattern of four holes. In some embodiments, the button is configured such that a top surface of the button is flush with a top surface of the main body when the button is seated in the first and/or second aperture. In some embodiments, first and second buttons are associated with respective first and second apertures.

In some embodiments, the button is configured so as to allow a user to secure one or more attachment member 50 to the main body. In some embodiments, the attachment member 50 can be sutures used for fixation and/or sutures sewn into tendon graft ends. In some embodiments, one or more attachment member 50 obviates any requirements for interference screw placement.

In some embodiments, the button is configured so as to facilitate coupling one or more attachment member 50 to the button, such as to an under surface of the button. In some embodiments, drilling larger clavicle tunnels to can be avoided by passing attachment members, such as sutures, from inferior to superior. In some such embodiments, the present invention enables the risk of clavicle fracture to be reduced by allowing for slightly smaller holes to be drilled if desired.

The present invention further includes a method of treating AC joint dislocations and other injuries associated with the clavicle by drilling bone tunnels through a third region of a clavicle of a patient, the third region of the clavicle being positioned between opposed first and second regions of the clavicle. In some embodiments, the method includes utilizing one or more positioning feature 150 of the clavicle plate 10 of the present invention to position the clavicle plate 10 relative to the clavicle 20. In some embodiments, the method further includes securing first and second portions of the clavicle plate to respective first and second regions of the clavicle such that a third portion of the clavicle plate, extending between the first and second portions of the clavicle plate, extends over the third region of the clavicle. In this way, the clavicle plate provides structural support to the clavicle, thereby reducing risk of fracture associated with drilling bone tunnels through the third region of the clavicle. In some embodiments, the method includes securing to the clavicle plate sutures used for fixation and/or sutures sewn into tendon graft ends. In some such embodiments, buttons associated with first and/or second apertures of the clavicle plate are utilized to assist with anchoring, wrapping, and/or grafting. In some embodiments, one or more fixation feature 115, such as a small aperture, is utilized to receive one or more fixation device 15, such as a suture. In some embodiments, a first and/or second aperture is utilized without a button to assist with anchoring, wrapping, and/or grafting.

The present invention further includes a method of treating clavicle fractures and other injuries associated with the clavicle by securing first and second portions of a clavicle plate of the present invention to respective first and second regions of the clavicle such that a third portion of the clavicle plate, extending between the first and second portions of the clavicle plate, extends over the fracture. In this way, the clavicle plate provides structural support to the clavicle, thereby allowing the clavicle to heal.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the inventions is by way of example, and the scope of the inventions is not limited to the exact details shown or described.

Although the foregoing detailed description of the present invention has been described by reference to an exemplary embodiment, and the best mode contemplated for carrying out the present invention has been shown and described, it will be understood that certain changes, modification or variations may be made in embodying the above invention, and in the construction thereof, other than those specifically set forth herein, may be achieved by those skilled in the art without departing from the spirit and scope of the invention, and that such changes, modification or variations are to be considered as being within the overall scope of the present invention. Therefore, it is contemplated to cover the present invention and any and all changes, modifications, variations, or equivalents that fall with in the true spirit and scope of the underlying principles disclosed and claimed herein. Consequently, the scope of the present invention is intended to be limited only by the attached claims, all matter contained in the above description and shown in the accompanying drawings shall be interpreted as illustrative and not in a limiting sense.

Having now described the features, discoveries and principles of the invention, the manner in which the invention is constructed and used, the characteristics of the construction, and advantageous, new and useful results obtained; the new and useful structures, devices, elements, arrangements, parts and combinations, are set forth in the appended claims.

It is also to be understood that the following claims are intended to cover all of the generic and specific features of the invention herein described, and all statements of the scope of the invention which, as a matter of language, might be said to fall therebetween.

What is claimed is:

1. A clavicle plate for reinforcing a clavicle of a patient, the plate comprising:
    a main body having opposed first and second portions extending from opposed ends of a third portion;
    a centerline mark that is configured to assist with placement of said main body with respect to a clavicle of a patient;
    first and second fastening means for securing respective first and second portions of said main body to respective first and second portions of the clavicle;
    first and second apertures associated with anatomical locations of respective conoid and trapezoid ligaments of the patient, the first and second apertures positioned within the third portion of said main body and being configured to assist with repairing respective conoid and trapezoid ligaments;
    a first fixation feature positioned posterior to the second aperture; and
    a second fixation feature positioned anterior to the first aperture,
wherein the third portion of said main body is adapted to extend over a third portion of the clavicle, and
wherein said first and second fixation features each comprise one or more small apertures and are adapted to engage with one or more fixation devices.

2. The plate of claim 1, wherein the first and second fastening means comprise respective first and second screw holes defined by respective first and second portions of said main body, said first and second screw holes being configured to receive respective screws having a diameter between 3.5 mm and 4.0 mm.

3. The plate of claim 1 further comprising a drill guide, wherein each of said first and second apertures is configured to interface with the drill guide for (a) positioning and orienting the drill guide relative to the clavicle, (b) facilitating the positioning and vectoring of respective first and second bone tunnels, and (c) assisting with drilling said respective first and second bone tunnels through the clavicle.

4. The plate of claim 1, further comprising a first button that is configured to interface with said first aperture, said first button being moveable between a seated configuration and an unseated configuration relative to said first aperture, wherein said first aperture and said first button define corresponding interface features.

5. The plate of claim 4, wherein said corresponding interface features include tapered walls such that said first aperture defines opposed top and bottom openings, said top opening being larger than said bottom opening.

6. The plate of claim 4, wherein said corresponding interface features include a non-circular shape such that said first button is prevented from rotating relative to the plate while the first button is in the seated configuration.

7. The plate of claim 6, wherein said first button is moved to the seated configuration by moving said first button in a first direction towards the clavicle and wherein said corresponding interface features include tapered walls such that movement of said first button in the first direction is limited to movement of said first button to the seated configuration.

* * * * *